United States Patent [19]

Winchell et al.

[11] 4,024,233
[45] May 17, 1977

[54] 99m-TECHNETIUM LABELED MACROAGGREGATED HUMAN SERUM ALBUMIN PHARMACEUTICAL

[75] Inventors: Harry S. Winchell, Lafayette; Morton Barak; Parmer Van Fleet, III, both of Walnut Creek, all of Calif.

[73] Assignee: Medi-Physics, Inc., Emeryville, Calif.

[22] Filed: July 24, 1974

[21] Appl. No.: 491,204

Related U.S. Application Data

[63] Continuation-in-part of Ser. No. 259,679, June 5, 1972, abandoned.

[52] U.S. Cl. .............................. 424/1; 252/301.1 R; 252/316
[51] Int. Cl.² .................. A61K 29/00; A61K 43/00
[58] Field of Search .................. 424/1; 252/301.1 R, 252/316

[56] References Cited

UNITED STATES PATENTS

| 3,663,685 | 5/1972 | Evans | 424/1 |
|---|---|---|---|
| 3,663,687 | 5/1972 | Evans | 424/1 |
| 3,725,295 | 4/1973 | Eckelmann et al. | 252/301.1 R |
| 3,803,299 | 4/1974 | Novel | 424/1 |
| 3,863,004 | 1/1975 | Wolfangel | 424/1 |
| 3,872,226 | 3/1975 | Haney et al. | 424/1 |

OTHER PUBLICATIONS

Benjamin, International Journal Applied Radiation and Isotopes, vol. 20, 1969, pp. 187–194.
Honda et al., Journal of Nuclear Medicine, vol. 11, No. 10, 1970, pp. 580–585.
Morcellet et al., Journal de Biologie et de Nucleairos, vol. 4, No. 17, May–June, 1969, pp. 16–18.
Berger et al., Isotopenpraxis, vol. 7, 1971, pp. 188–189.
Eckelman et al., Radiology, vol. 102, Jan. 1972, pp. 185–186.
Robbins et al., Journal of Nuclear Medicine, vol. 13, No. 6, 1972.

*Primary Examiner*—Benjamin R. Padgett
*Assistant Examiner*—Christine M. Nucker
*Attorney, Agent, or Firm*—Samuel L. Welt; Bernard S. Leon; R. Hain Swope

[57] ABSTRACT

A reagent comprising macroaggregated human serum albumin having dispersed therein particles of stannous tin and a method for instantly making a labeled pharmaceutical therefrom, are disclosed. The labeled pharmaceutical is utilized in organ imaging.

3 Claims, No Drawings

99m-TECHNETIUM LABELED MACROAGGREGATED HUMAN SERUM ALBUMIN PHARMACEUTICAL

CROSS-REFERENCE TO RELATED APPLICATIONS

The present application is a continuation-in-part of U.S. patent application Ser. No. 259,679, filed June 5, 1972, now abandoned.

BACKGROUND OF THE INVENTION

It is known that radionuclidically labeled particulate material of a sufficient size (10 $\mu$m diameter) administered into the afferent blood supply of a given organ will lodge in the capillary bed of that organ. When such particulate material has been uniformly mixed with the blood afferent to the organ prior to reaching the capillary bed, the distribution of the radionuclide in the organ reflects the capillary blood flow to that organ. Thus, radionuclidically labeled particulate materials have been successfully used in scintigraphic evaluation or perfusion abnormalities of the lungs and other tissues such as occur in infarction and various types of vascular occlusion with or without infarction.

Macroaggregated human serum albumin labeled with iodine-131 has been widely used for the above described purposes. However, radionuclides such as technetium-99m are preferred over iodine-131 in scintigraphic studies because of their lower radiation dose and greater compatibility of their gamma emission with existing radiation detection devices. One procedure described in the literature for the preparation of technetium-99m-labeled macroaggregated human serum albumin comprises initially labeling unaggregated human serum albumin with technetium-99m using either Fe(III) and ascorbic acid, or Sn(II) followed by heat denaturation and macroaggregation of the technetium-99m-labeled albumin. Such procedures require the availability of skilled radiopharmacists at the site of use of the preparation to prepare the material prior to use. Moreover, the short physical half-life of the technetium-99m does not allow sufficient time to completely qualify the product prior to use. Such qualification includes assessment of particle size distribution, particle density, degree of binding of the technetium-99m to the particles, in vivo distribution pattern of the labeled particles in test animals, and determination of apyrogenicity, sterility and general safety of the product. Moreover, in preparations in which the human serum albumin is labeled with technetium-99m prior to its macroaggregation, there is a tendency for the technetium-99m label to come off or elute from the product thereby yielding undesirable unbound activity. An approach to the solution of this problem in the past has been to react heat denatured albumin microspheres with technetium-99m using Fe(II) and ascorbic acid. Such techniques are time consuming and require special apparatus. The tendency for technetium-99m to elute from such products remains a significant factor, such that the free technetium-99m must be washed from the labeled product shortly before administration thereof to the patient.

An additional method of formulating technetium-99m into a preparation suitable for the scintigraphic evaluation of perfusion abnormalties known in the art comprises binding the technetium-99m in inorganic precipitates of iron or tin. Such inorganic precipitates suffer from a lack of precise definition of particle size distribution as the particle size will vary as a function of concentration of ingredients and passage of time after preparation. Generally, the higher the concentration of ingredients and the longer the time after preparation the larger is the mean particle size. Moreover, long-term retention of the inorganic precipitate in the lung has been demonstrated for certain such preparations, suggesting the possibility of undesirable long-term toxicity.

In accordance with the present invention, a preparation for studying capillary perfusion of tissues is provided which is free of the disadvantages of prior art preparations noted above. Thus, preparations of the present invention can be completely qualified prior to distribution because they are stable for well over 6 months at room temperature or under refrigeration. The stable preparations of the present invention are further characterized by being amenable to virtual quantitative labeling with technetium-99m by mixing therewith without the need of washing or other preparative procedures. The technetium-99m is firmly bound and does not usually elute from the particles of the preparations of the invention for over 24 hours after labeling.

DETAILED DESCRIPTION OF THE INVENTION

The present invention pertains to a stable macroaggregate HSA-tin (II) colloid reagent sized for evaluation of capillary perfusion of organs such as the lung. Further, the invention pertains to a simple method of utilizing the reagent to prepare a labeled macroaggregate with 99m-technetium pertechnetate saline solutions such as are generally available. The labeled product is characterized by a stable particle size well suited for evaluation of capillary perfusion of organs such as the lung and by having the 99m-technetium firmly and quantitatively bound to the tin (II) particles distributed throughout the macroaggregated HSA.

The improved base reagent of the present invention is comprised of complexes of microcolloidal stannous tin distributed throughout a HSA macroaggregate and embedded therein, the macroaggregates being sized for evaluation of capillary perfusion of organs such as the lung. The makeup of the complexes of the invention has been observed by oxidizing the dispersed tin (II) particles and examining the resulting particulate complex microscopically. The 99m-technetium labeled macroaggregated HSA prepared from the reagent of the present invention is further an improvement over prior products of a similar nature in that it is not hard and therefore clears the lung rapidly after lodging there for a sufficient time to permit useful scintigraphic imaging.

The reagent of the present invention comprises a physiological suspension of a particulate complex of macroaggregated HSA and stannous tin. The reagent is prepared by dispersing human serum albumin in normal saline which has been buffered to a pH from about 5.2 to 5.6. Suitable buffering agents are those commonly recognized in the art such as, for example, an acetate buffer pair, i.e., acetic acid/sodium acetate, a phosphate buffer pair, i.e., sodium acid phosphate/disodium phosphate and the like. Of these, the phosphate buffer is preferred. The resulting dispersion is then rapidly heated in a bath having a temperature of from about 105° C to about 110° C. to coagulate the albumin into a macroaggregate dispersion. After the macroaggregate dispersion has been formed, the mixture is removed from the heat and stannous chloride in pyrogen-free water is added thereto. The concentration of stannous chloride in said solution can be from about 1 to about 10mM. Cooling is maintained with stirring for a short time, i.e., about 10 to 20 minutes, after which it is accelerated by an ice bath to ambient temperature. During this process, the tin colloid complexes with and becomes entrapped throughout each macroaggregated HSA particle. The preparation is then filtered to remove particles in excess of 100 microns, washed to remove particles of less than 10 microns and packaged in sufficient normal saline to yield a particle density of, preferably 300,000 to 600,000 particles/ml., all utilizing aseptic techniques. It is critical to the stability of the reagent of the invention that the containers therefor be scrupulously cleared and be purged with nitrogen before filling so as to remove all traces of oxygen therefrom. Prior to packaging it is preferred to add a suitable quantity of a preservative to the reagents of the invention. Suitable preservatives include, for example, benzyl alcohol, the parabens, thimerosal and the like. Of these benzyl alcohol in a concentration of 2% weight to volume based on the total reagent is preferred. It is also preferred to add to the wash liquid a concentration of the preservative approximating that in the finished reagent.

Packaged reagent made by the above procedures has a shelf lift of at least six months at room temperature or under refrigeration. The suspended particulate complex of the described reagent and ultimate pharmaceutical produced therefrom is predominantly, i.e., over 90%, in the range of 10 to 90 microns in size. Because the particles are somewhat oval in shape it has been found that up to 1% between 100 and 150 microns at their largest dimension may pass the filter and be found in the product. Substantially no particles are greater than 150 microns at their largest dimension. The particle size can, however, be easily established at any preselected size range as is recognized in the art. In preparing the complex for imaging, the reagent is simply added to 99m-technetium pertechnetate saline solution to form an efficiently labeled complex wherein the radioactivity is firmly bound and does not easily elute therefrom. The procedure required to prepare the labeled complex for injection comprises steps exemplified as follows.

First, a quantity of 99m-technetium pertechnetate in normal saline solution sufficient to provide the amount of radioactivity desired for administration to a single patient is drawn into a syringe or suitable container using aseptic technique. The quantity required is generally about 2–3mCi. Second, an ampule of the tin (II)-macroaggregated HSA reagent is opened aseptically and enough reagent is drawn into the same syringe or container containing the pertechnetate to result in a final proportion of about 3 parts by volume of reagent to 1 part by volume of pertechnetate solution. The 99m-technetium is reduced by the stannous ions and instantly labels the particulate tin (II)-macroaggregated HSA complex. Third, a small volume of air is drawn into the syringe and the syringe shaken well for 10 seconds to assure complete mixing. Finally, the now efficiently labeled macroaggregate is allowed to incubate at room temperature for a few minutes. It then can be intraveneously injected slowly into the patient.

The labeling is efficient resulting in over 90% retention of activity in the lungs so that no purification is necessary. The labeling efficiency is generally unaffected by the concentration of reagent and the labeling produces substantially no change in the particle size range of the reagent.

The following examples and the described procedures are for illustrative purposes only. It will be apparent to those skilled in the art that both may be modified within the scope of the invention as defined in the following claims.

EXAMPLE 1

A total of 21 ml. of a 0.67 molar phosphate buffer and sufficient normal saline solution to achieve a total volume of two liters were heated to a boil in a macroaggregation flask. The flask was removed from the heat and oxygen purged from the mixture as it cooled by passing nitrogen gas through it. The pH of the solution was checked to assure that it was between pH 5.2 and 5.6. The flask was then sealed and autoclaved. After the solution had cooled to room temperature, one gram of human serum albumin (salt poor, U.S.P.) as a 250 mg/ml solution was thoroughly dispersed therein. The flask was then immersed in a brine bath at 108° C. and maintained with stirring for 8 minutes to coagulate the albumin into a macroaggregate dispersion.

After formation of the dispersion, the flask was removed from the bath, 200 ml. of a 10 mM solution of stannous chloride in pyrogen-free water was added thereto and the mixture was allowed to cool with constant stirring. After the mixture had cooled for ten minutes, it was placed in an ice bath and brought to room temperature with continued stirring.

The contents of the flask were then passed with continuous stirring successively through a blood administration filter (pore size 200 to 260 microns) and a stainless steel filter (pore size 100 microns) into a sterile settling flask purged with filtered nitrogen. The settling flask was stored at 4° C. until the suspended particles settled. The supernatant liquid was then withdrawn and replaced utilizing aseptic techniques with a wash solution of 2% by weight benzyl alcohol in normal saline. The particles were resuspended, again allowed to settle at 4° C. and the washing procedure repeated. After washing, a sufficient amount of the benzyl alcohol solution was added to achieve a final particle density of about 500,000/ml. The resulting suspension was then packaged in nitrogen purged sterile ampules from free oxygen and other oxidizing agents.

EXAMPLE 2

The procedure of Example 1 was repeated utilizing as the buffer 200 ml. of a 0.1N acetate buffer and, as the preservative, a sufficient amount of a 1/5000 solution thimerosal to achieve a concentration of 1.33 parts thereof to 10,000 parts of the final reagent.

We claim:

1. A stable reagent suitable for the preparation of a 99m-technetium labeled pharmaceutical for scintigraphic organ imaging by the addition of a solution of 99m-technetium pertechnetate comprising an aqueous suspension of macroaggregated human serum albumin sized for such imaging having distributed throughout particles of colloidal stannous tin, said particles of colloidal stannous tin being entrapped throughout each particle of said macroaggregates.

2. A method of preparing the reagent of claim 1 which comprises:

a. heating a dispersion of human serum albumin in physiological saline to coagulate said albumin into a macroaggregate;
b. mixing with said warm dispersion a colloid of hydrolyzed stannous chloride in pyrogen free water; cooling said mixture thereby entrapping particles of colloidal stannous tin throughout each particle of said macroaggregate;
d. filtering the resulting dispersion to remove therefrom substantially all particles larger than 100 microns; and
e. washing said dispersion to remove therefrom substantially all particles smaller than 10 microns.

3. A 99m-technetium labeled pharmaceutical for scintigraphic organ imaging comprising a physiological suspension of macroaggregated human serum albumin sized for said imaging having distributed throughout particles of colloidal stannous tin, said tin particles being entrapped throughout each particle of said macroaggregate, said macroaggregates being labeled with 99m-technetium.

* * * * *